United States Patent [19]

Chiron et al.

[11] Patent Number: 5,945,075
[45] Date of Patent: Aug. 31, 1999

[54] PROTECTIVE BOX FOR STERILIZING AND PRESERVING ORGANIC MATTER OR MATERIAL AND ASSEMBLY APPLYING SAME

[75] Inventors: Philippe Charles Chiron, Toulouse; Jean Collomb, Portes les Valence; Charles Picault, Sainte Foy les Lyons, all of France

[73] Assignee: Merck Biomaterial France, Charnoz, France

[21] Appl. No.: 08/608,721

[22] Filed: Feb. 29, 1996

[30] Foreign Application Priority Data

Mar. 1, 1995 [FR] France ................................ 95 02656

[51] Int. Cl.⁶ .............................. B01L 3/00; A61L 2/04
[52] U.S. Cl. ........................ 422/300; 422/102; 206/592; 220/371
[58] Field of Search ................... 422/300, 302, 422/102; 206/521, 521.6, 523, 588, 592, 594; 220/371; 435/284.1

[56] References Cited

U.S. PATENT DOCUMENTS

| | | | |
|---|---|---|---|
| 3,819,081 | 6/1974 | Runte | 206/592 X |
| 4,637,919 | 1/1987 | Ryder et al. | 422/310 X |
| 4,872,563 | 10/1989 | Warder et al. | 206/523 X |
| 4,881,562 | 11/1989 | Wright et al. | 206/523 X |
| 5,232,600 | 8/1993 | Degen et al. | 210/640 |
| 5,236,088 | 8/1993 | Dhority et al. | 206/523 X |
| 5,681,740 | 10/1997 | Messier et al. | 435/284.1 |

FOREIGN PATENT DOCUMENTS

| | | |
|---|---|---|
| 0 152 544 A3 | 8/1985 | European Pat. Off. . |
| 0 584 484 A1 | 3/1994 | European Pat. Off. . |
| WO 87/05520 | 9/1987 | WIPO . |

*Primary Examiner*—Elizabeth McKane
*Attorney, Agent, or Firm*—Bacon & Thomas

[57] ABSTRACT

This invention relates to a protective box for the sterilization of organic material. The box includes a box body adapted to receive and immobilize a packing, a box lid fitting on the body and forming, internally, at least one protuberance for cooperation with the capsule of the packing, removable connecting means designed to bring the body and the lid relatively closer axially when the box is closed, and at least one opening provided in the body and/or the lid to place the inner volume of the closed box in relation with the ambiant medium. The invention is more particularly applicable to bone transplants.

10 Claims, 1 Drawing Sheet

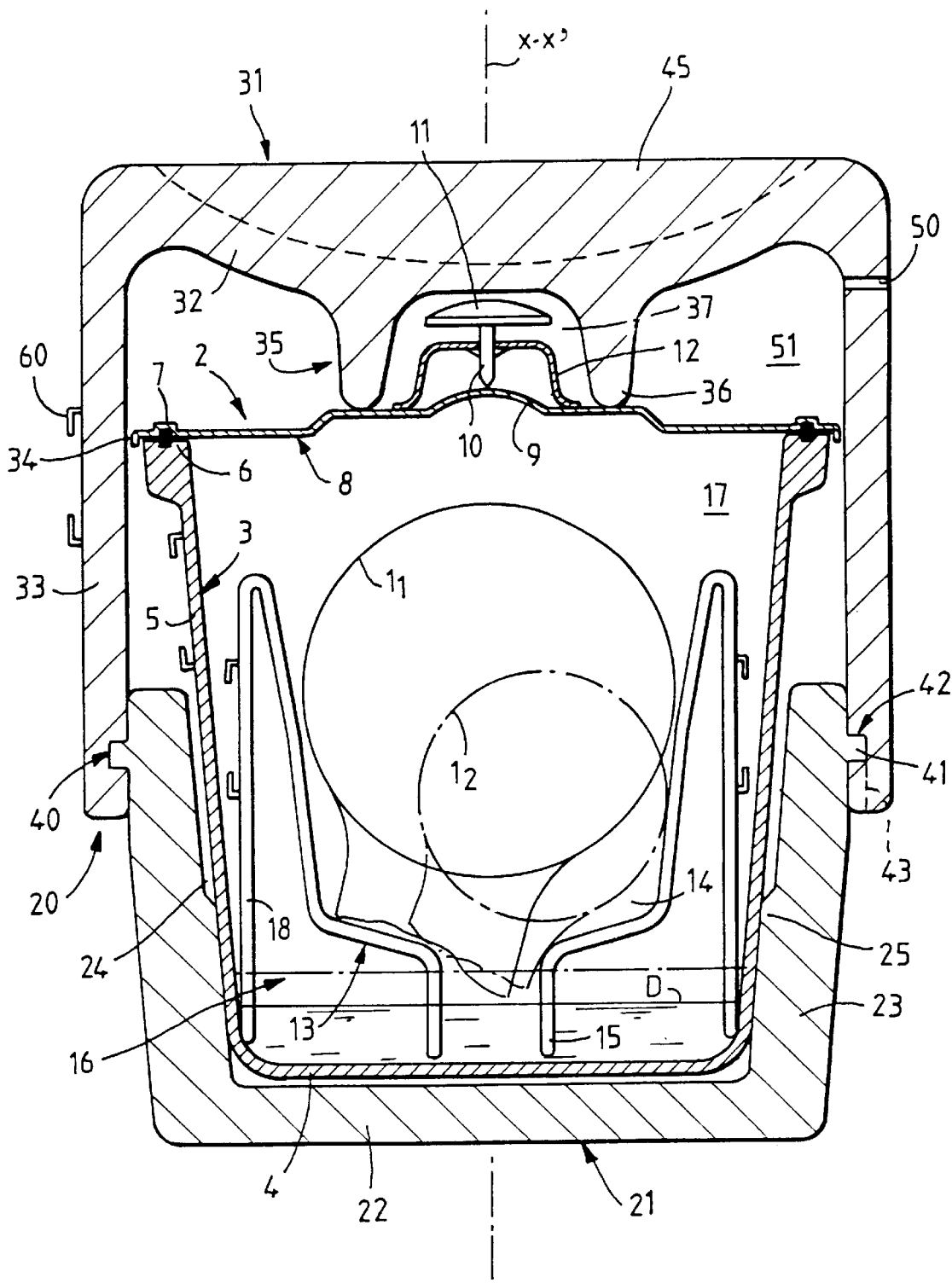

5,945,075

PROTECTIVE BOX FOR STERILIZING AND PRESERVING ORGANIC MATTER OR MATERIAL AND ASSEMBLY APPLYING SAME

FIELD OF THE INVENTION

The present invention relates to the preservation of organic matters and materials, with a view to allowing subsequent use thereof in complete safety.

The invention may concern different domains of application, such as that of preservation of food products or the conservation of organic materials re-usable in the pharmaceutical, medical, biological, etc. . . . domain.

BACKGROUND OF THE INVENTION

The preservation of organic matters or materials has already formed the subject matter of relatively numerous publications describing various methods of conservation.

By way of indication, mention may be made of incubation as taught by Application EP-0.584.484, cryopreservation, lyophilization, and sterilization.

The first method does not appear to satisfy the requirements of elimination of the risks of residual contamination of the matter.

The following two methods present the drawback of employing heavy and relatively expensive processes which, furthermore, do not provide absolute safety as to the risks of residual contamination by micro-organisms or by viruses.

The process of sterilization may include different methods, such as the application of radiations, the application of ethylene oxide or sterilization by wet heat.

The application of radiations, of the X, Gamma or beta type, involves considerable equipment and is delicate to carry out. Furthermore, such radiations are the origin of an alteration of the properties of the organic matters whose re-use may consequently be partly hampered and even hindered. Moreover, the cost of carrying out such a method is high.

Sterilization by ethylene oxide presents the drawback of representing for the personnel a risk, either direct, or via the secondary reaction products, such as ethylene-glycol and ethylene-chlorohydrin, products reputed to be toxic.

Sterilization by wet heat appears to be an interesting technique, due to the possibility that it offers of being successfully carried out, employing relatively simple technical means, with a relatively low energy consumption.

However, the problem raised for carrying out such a method is to have equipment available which enables the process of sterilization by the wet method to be successfully carried out, as is known, by means of an autoclave and a process of sequential application of well determined temperatures and which, moreover, ensures a preservation of the matter or of the sterilized material under conditions of absolute safety allowing storage, transport, as well as a possible re-use under optimum conditions.

Another problem is that of conserving the organic matter or material having to be sterilized, being visually sure that the sterilization having taken place corresponds exactly to the operational process having been conducted.

It may be considered that, at the present time, the known technique does not furnish material adapted to respond to the requirements set forth hereinabove.

It is an object of the present invention to overcome these shortcomings by proposing a protective box for sterilization and preservation which makes it possible to perform the above double function for a sterilizing packing, of known conception, so that the function of sterilization can be performed under optimum conditions and the function of storage, manipulation and transport can be performed while ensuring an efficient protection of the packing against the risks of untimely opening, but also against shocks, bangs and even drops which may result from the manipulation, storage, transport operations.

SUMMARY OF THE INVENTION

To that end, the protective box for sterilizing and packing organic matter or material is characterized in that it comprises:

a box body adapted to receive and immobilize a packing, a box lid adaptable on the body and forming, internally, at least one protuberance for cooperation with the capsule of the packing, removable connecting means designed to bring the body and the lid relatively closer axially when the box is closed, and at least one opening provided in the body and/or the lid to place the inner volume of the closed box in relation with the ambiant medium.

The invention also has for its object an assembly for sterilizing and preserving organic matter or material, characterized in that it is composed of a packing comprising a jar and a perforatable capsule for tight closure, and of a protective box.

BRIEF DESCRIPTION OF THE DRAWINGS

The invention will be more readily understood on reading the following description with reference to the accompanying drawings, in which:

The single FIGURE is a section in elevation of the object according to the invention.

DESCRIPTION OF PREFERRED EMBODIMENT

Referring now to the drawing, the protective box according to the invention is designed to allow sterilization and preservation of organic matter or material such as 1, contained in a packing such as 2. The matter 1 is represented in the form of bone transplants, for example femur ends, of which two sizes are illustrated and designated by references $1_1$ and $1_2$. It must be considered that the object of the invention may be applied to any other organic matter or material and may find use in the domain of food or of organic tissues in the pharmaceutical, biomedical, etc. . . . domain.

With a view to sterilizing and preserving a material such as 1, the packing 2 comprises a jar 3 of truncated form, upwardly open from a bottom 4. The jar 3 comprises a peripheral wall 5 whose upper edge defines an annular bearing surface 6 on which abuts, via an O-ring 7, a capsule 8 presenting, in its central part coinciding with the axis xx' of revolution of the jar, a bulb 9 intended to be pierced via a perforator 10. According to the invention, the perforator 10 is constituted by the point of a knob 11 which is borne by a bridge 12 rising above capsule 8.

To allow sterilization and preservation of the matter or material 1, the jar internally contains a beaker or a strainer 13 defining a housing 14 for receiving the material 1. The beaker or strainer 13 presents in its lower part mounts 15 adapted to abut on the bottom 4, to define a compartment 16 adapted to receive a dose D of an appropriate liquid product adapted to supply saturated vapour when the process of sterilization is started and continued.

The beaker 13 or the strainer presents a perforated or otherwise open-worked bottom so as to establish communication between the compartment 16 and the housing 14 which is open in its upper part to communicate likewise with the inner volume 17 defined by the jar 3. The periphery of the beaker 13 is provided with outer legs 18 which are provided to cooperate partly with the bottom 4 and partly with the peripheral wall 5, so as elastically to ensure centering of the beaker 13 inside the volume 17 and protect the matter or material 1 from any contact with the peripheral wall 5.

A packing of the above type is provided to be subjected to a sterilization phase employing, in known manner, sequences of heating and placing in vacuo, so as to establish a saturated wet vapour in the volume 17, with temperature conditions close to 120° C. and a duration of exposure of the order of 20 minutes.

To carry out such a sterilization process successfully, the invention recommends employing a protective box generally designated by reference 20. The protective box comprises a box body 21 constituted by a bottom 22 bordered by a peripheral wall 23, so as to define a housing 24 adapted to receive the packing 2 and, more particularly, the jar 3. According to the invention, the housing 24 is provided with means adapted to ensure transverse and axial immobilization of the packing 2, while maintaining, preferably in this state, the bottom 4 of the jar 3 at a distance from the bottom 22 of the box body 21. Such means designate by reference 25 are for example constituted by excess thicknesses which are at least local, preferably but not exclusively axial, projecting from the inner face of the peripheral wall 23, so as to present a convergence towards the bottom 2. In this way, the jar 3 may be inserted in housing 24 and be wedged therein in a state of axial and transverse immobilization in which, as shown in the drawing, the bottom 4 is placed at a distance from the bottom 22.

To perform this function, as well as that of protection, the box body 21 may be made of any material allowing a certain elastic or plastic deformation. By way of example, the material constituting the box body 21 may be expanded polystyrene or a similar material having been developed into a more or less compact foam with open or closed cells.

According to another characteristic of the invention, the protective box 20 also comprises a box lid 31 which is made in the manner of an upturned jar to comprise a top 32 extended by a skirt 33 adapted to fit over the peripheral wall 23. The skirt 33 presents such a height that it envelops that part of the packing 2 rising beyond the upper edge of the peripheral wall 23, as well as a section of passage which is greater than the diameter of the capsule 8. Consequently, the fit of the body lid 31 leaves a space or gap 34 between the inner peripheral wall of the skirt 33 and the peripheral edge of the capsule 8. The body lid 31 is made of a material identical or similar to that of the box body 21 to perform the same function of protection.

The top 32 comprises on its inner face a protuberance 35 which is intended to abut on the capsule 8 when the assembly is closed, resulting from the association of the box body 21 with the box lid 31. The protuberance 35 is preferably constituted by an annular rib 36 concentric to the axis of revolution xx' and which defines a cavity 37 for fit and protection of the knob 11 and the bridge 12. The cavity 37 is designed to allow insertion of the perforator 10 whatever its form and in its inactive state of non-perforation, as shown in the accompanying drawing, when the rib 36 abuts on the caspule 8.

The protective box described hereinabove is completed by the presence of means 40 for removable connection between the lid 31 and the body 21. The means 40 are in all cases chosen so as to bring the body 21 and the lid 31 relatively closer axially, when the box is closed, this having for its effect to apply or press the protuberance 35 on the capsule 8 in abutment against the jar 3 immobilized in the body 21. By way of illustration and non-limiting example, the means 40 may be constituted by ramps or helicoidal threads 41 adapted to cooperate with grooves 42 in which the ramps 41 may be engaged by passing in undercuts 43.

Means 40 ensure a removable connection by screwing or the like and, to that end, the top 32 is advantageously shaped to present a handle 45 or the like arranged in the form of a transverse beam projecting with respect to the top 32 but inscribed in the envelope of the jar that the box lid 31 defines.

According to the invention, the box further comprises at least one opening, slot or passage 50 made in the box body 21 or in the box lid 31, and preferably in the skirt 33, so as to establish permanent communication between the ambient medium and the inner volume 51 which is formed around the packing 2 by the association of the body 21 and of the lid 31 together forming the protective box 20.

To employ the object of the invention for an operation of sterilization and preservation, the jar 3 is charged with the dose D then with the matter 1 placed in the housing 14 of the beaker 13. The jar 3 is then placed in position in the housing 24 to be transversely and axially immobilized therein. The capsule 8 is then placed on the peripheral area 6 to allow positioning of the lid 31 like a cap, the latter exerting, by the protuberance 35, by the cooperation of the ramps 41 and the grooves 42, the action of pressing maintaining the capsule 8 on the jar 3. In this state, the assembly may be manipulated and subjected to a sterilization operation without any risk, being given that the packing 2 is protected against knocks, shocks and deterioration, the matter 1 is disposed inside the closed jar 3 and the capsule 8 is maintained in place via the lid 31.

The development of a process of sterilization allows, via the openings 50, the placing of volume 51 and volume 17 in vacuo and the rise in temperature producing or generating in volume 17 the saturated wet vapour occupying the whole useful volume, as well as the housing 14 for subjecting the matter 1 to the known phase of sterilization.

At the end of sterilization, the capsule 8 is applied by atmospheric pressure on the jar 3 which is thus hermetically closed in a secure state ensuring preservation of the matter 1. In fact, the protective box provides efficient protection of the elements constituting the packing 2 and protects the capsule 8 from any risk of deterioration or action of thrust or traction applied in particular on the edge 34 and capable of leading to untimely opening.

The protective box therefore allows manipulation of the assembly, storage, transport, without any risk of deterioration and denaturation of the state of sterilization produced.

As the case may be and as needed, the protective box also allows a visual assessment of the packing 2 and its contents, being given that it suffices to unscrew or displace the lid 31 and the body 21 relatively by rotation about axis xx', to allow an opening giving visual access by reason of the at least translucent or most generally transparent constituent material used for constituting the jar 3.

When it is desired to have access to the matter 1, with a view to using it, it suffices, after removing the lid 31, to exert a thrust on the knob 11 for the perforator 10 to pierce the capsule 8 at the level of bulb 9 and re-establish atmospheric pressure in the volume 17.

The lid or the box 21 may comprise on the outer surface means such as 60 for insertion and hold of means identifying the contents and conditions of sterilization imposed on the assembly constituted by the packing 2 and the box 20.

The invention is not limited to the example described and shown, as various amendments may be made thereto without departing from its scope.

What is claimed is:

1. A protective box for sterilization and preserving organic matter or material contained in a packing formed by a jar and capsule which hermetically closes said jar when a vacuum is created inside the packing; wherein said box comprises:

a box body adapted to receive and immobilize the packing, a box lid fitted on the body and forming, internally, at least one protuberance for cooperation with the capsule of the packing in order to at least maintain the capsule on the jar before sterilization, means for connecting said body and said lid in a removable manner and for bringing the body and the lid relatively closer axially when the box is closed, and at least one opening provided in the body and/or lid to place the inner volume of the closed box in fluid communication with the ambient medium in order to allow the placing in vacuo of the volume inside the packing and the volume inside the protective box during sterilization.

2. The protective box of claim 1, wherein the box body comprises a bottom and a peripheral wall defining an open housing for receiving and immobilizing a packing.

3. The protective box of claim 1, wherein the box body comprises means for transversely and axially immobilizing a packing at a distance from the bottom of the box body.

4. The protective box of claim 3, wherein the immobilization means are formed by at least local excess thicknesses presented by the inner face of the peripheral wall of the box body.

5. The protective box of claim 1, wherein the box lid is in the form of a cover and comprises a top bordered by a skirt adapted to surround the packing and its capsule at a distance.

6. The protective box of claim 1, wherein the box lid comprises on the inner face of its top a protuberance constituted by an annular rib adapted, when the box is closed, to press the capsule on the jar and to fit this latter in the housing of the body of the box.

7. The protective box of claim 6, wherein the box lid is in the form of a cover and comprises a top bordered by a skirt adapted to surround the packing and its capsule at a distance and wherein the annular rib is concentric to the axis of revolution of the skirt and defines a cavity for fit and protection of a capsule perforator.

8. The protective box of claim 1, wherein the means for connecting said body and said lid in a removable manner and for bringing the body and the lid relatively closer axially when the box is closed are of the type incorporating helicoidal thread and the top of the lid forms a handle for griping and rotating the lid with respect to the body.

9. An assembly for sterilizing and preserving organic matter or material, wherein said assembly comprises the protective box of claim 1 with said packing contained therein, and said packing comprises:

a jar and a perforatable capsule thereon adapted to hermetically close the jar when a vacuum is created inside the packing.

10. The assembly of claim 9, wherein said protuberance defines a cavity and the capsule of the packing bears a perforator which is disposed in the cavity for fit and protection.

* * * * *